United States Patent
Woods

(10) Patent No.: US 9,265,604 B2
(45) Date of Patent: Feb. 23, 2016

(54) DEVICE FOR USE IN DELIVERY OF OPHTHALMIC LENSES

(71) Applicant: Duckworth and Kent Limited, Hertfordshire (GB)

(72) Inventor: Stephen Paul Woods, Hertfordshire (GB)

(73) Assignee: Duckworth and Kent Limited (GB)

( * ) Notice: Subject to any disclaimer, the term of this patent is extended or adjusted under 35 U.S.C. 154(b) by 0 days.

(21) Appl. No.: 14/476,018

(22) Filed: Sep. 3, 2014

(65) Prior Publication Data

US 2015/0066044 A1    Mar. 5, 2015

(30) Foreign Application Priority Data

Sep. 4, 2013  (GB) .................................. 1315707.8
Aug. 20, 2014 (GB) .................................. 1414832.4

(51) Int. Cl.
*A61F 2/16*       (2006.01)

(52) U.S. Cl.
CPC ............. *A61F 2/1667* (2013.01); *A61F 2/1672* (2013.01); *A61F 2/1678* (2013.01)

(58) Field of Classification Search
CPC .............................. A61F 2/1667; A61F 2/1678
See application file for complete search history.

(56) References Cited

U.S. PATENT DOCUMENTS

| 4,744,790 | A | 5/1988 | Jankowski et al. |
| 5,800,442 | A | 9/1998 | Wolf et al. |
| 6,059,791 | A | 5/2000 | Chambers |
| 6,267,768 | B1 | 7/2001 | Deacon et al. |
| 2004/0186484 | A1 | 9/2004 | Ryan |
| 2005/0192541 | A1 | 9/2005 | Novacek |
| 2006/0229633 | A1 | 10/2006 | Shepherd |
| 2006/0235429 | A1 | 10/2006 | Lee et al. |
| 2009/0112223 | A1 | 4/2009 | Downer |
| 2010/0217274 | A1 | 8/2010 | Lee et al. |
| 2012/0022548 | A1 | 1/2012 | Zacharias |
| 2013/0006259 | A1 | 1/2013 | Sanger |

FOREIGN PATENT DOCUMENTS

| EP | 1728488 | 6/2006 |
| GB | 2501109 | 10/2013 |
| WO | WO 2007/080868 | 7/2007 |
| WO | WO 2011/126144 | 10/2011 |

*Primary Examiner* — Gregory Anderson
(74) *Attorney, Agent, or Firm* — Baker & Hostetler LLP

(57) ABSTRACT

The actuator (see FIG. 2) comprises a barrel 16 and a plunger 22 received within the barrel. A clutch mechanism 54 is operable between the plunger and the barrel. In the engaged condition of the clutch, the plunger is advanced by rotation relative to the barrel. An axial load on the plunger disengages the clutch mechanism, allowing the plunger to be advanced axially while rotating the driven member 60. Two-handed or one-handed operation is therefore possible. A freely rotatable collar 27 on the plunger allows the plunger to be returned to its retracted position with a linear rearward movement while allowing rotation of the plunger. A resilient ring 35 mounted in a cross-passage 32 in a bush 28 at the forward end of the plunger provides a measured degree of frictional resistance to the plunger returning under its own weight to the retracted position. The ring may be replaced by a C-shaped resilient element (see FIG. 13). The actuator can be used in combination with a lens delivery device (see FIGS. 1 and 2).

5 Claims, 10 Drawing Sheets

DEVICE FOR USE IN DELIVERY OF OPHTHALMIC LENSES

CROSS-REFERENCE TO RELATED APPLICATIONS

This application claims priority to GB Application No. 1315707.8, filed Sep. 4, 2013 and GB Application No. 1414832.4, filed Aug. 20, 2014, the disclosures of which are incorporated herein by reference in their entirety. This application is also related by subject matter to U.S. application Ser. No. 13/859,784, filed Apr. 10, 2013, which is also incorporated herein by reference in its entirety.

The present invention relates to the delivery of ophthalmic lenses.

Intraocular lenses are implanted into the eye through very small incisions in the eye, usually in the cornea, the lenses being rolled into a spiral or cylindrical shape prior to delivery.

Delivery can be carried out using a delivery device which is controlled manually by a surgeon, employing either a one-handed or a two-handed technique. The one-handed technique usually involves delivery of a lens by depression of a plunger by the surgeon to progress the lens through the device and into the eye. This offers the advantage of freeing the surgeon's other hand for other actions. The two-handed technique of lens delivery usually involves delivery of a lens by rotation of a threaded plunger by the surgeon to produce linear motion in order to progress the lens through the device and into the eye. This technique offers the advantage of greater control of the delivery but with the disadvantage restricting the surgeon's freedom to perform other tasks using his other hand.

Regardless of the technique, or combination of techniques, used, it is important that the surgeon be able to maintain full control over the delivery device, both during and after the lens-insertion phase of the procedure being carried out.

The present invention provides a device for use in delivery of ophthalmic lenses, the device comprising a barrel, a plunger receivable in the barrel and movable between a first, withdrawn position and a second, more advanced position and coupling means providing a screw-threaded connection between a portion of the plunger and the barrel, whereby the plunger rotates relative to the barrel in moving from its second to its first position, the plunger having a portion which is rotatable relative to the connection portion of the plunger and is engageable manually by a user for linear movement in the withdrawal direction whilst allowing rotation of the plunger relative to the barrel.

Such a device allows a surgeon to return the plunger after a lens-insertion procedure quickly and easily to its withdrawn position by a simple linear manual action.

Preferably the rotatable portion has at least one outwardly-extending portion for manual engagement by a user, the outwardly-extending portion more preferably comprising a collar extending around the plunger.

Advantageously, the plunger comprises a terminal head portion of larger cross-section than that of the plunger and the rotatable portion is located adjacent the head portion, the rotatable portion preferably being movable into abutment with the head portion in order to urge the plunger in the direction from the second to the first position.

The invention also provides a device for use in delivery of ophthalmic lenses, the device comprising a barrel, a plunger receivable in the barrel and moveable between a first, withdrawn position and a second, more advanced position, the plunger having a portion which contacts the interior of the barrel and comprises a resilient member which is carried by the plunger and lies in a plane transverse to the direction of relative movement of the plunger and the barrel, one or more outer surface portions of the resilient member together extending over less than all of the periphery of the plunger and providing the said contact with the barrel.

Such a device can reduce, or avoid altogether, any tendency for the plunger to "drop-back" under its own weight into the first position when released.

Preferably, the resilient member is annular and, more preferably, is received in a transverse passageway in the plunger.

Further, the invention provides a device for use in delivery of ophthalmic lenses, the device comprising a barrel, a plunger receivable in the barrel and moveable between a first, withdrawn position and a second, more advanced position, the plunger having a portion which contacts the interior of the barrel and comprises a resilient annular member which is carried by the plunger and lies in a plane transverse to the direction of relative movement of the plunger and the barrel, an outer surface of the annular member providing the said contact with the barrel and the annular member being received in a transverse passageway in the plunger.

Such a device can also reduce, or avoid altogether, any tendency for the plunger to "drop-back" under its won weight into the first position when released.

Conveniently, the resilient member lies in a plane substantially perpendicular to the said direction of relative movement.

Advantageously, the resilient annular member protrudes from respective opposite ends of the passageway to provide the contact with the barrel.

The annular member may be retained in the passageway by contact between the portions of the plunger and respective portions of the annular member intermediate the end portions.

Preferably, the annular member is circular in plan in its relaxed condition, more preferably, it is resiliently deformed into an oval shape in plan and its protruding ends are at opposite ends of its major axis.

In one arrangement, a single resilient member extends around a respective portion of the periphery of the plunger.

In any arrangement, the resilient member may lie in a plane substantially perpendicular to the said direction of relative movement.

The resilient member may be C-shaped.

Preferably, the resilient member has a laminated structure, an inner layer of which provides a desired degree of resilience and an outermost layer provides a desired degree of friction with the inner surface of the barrel.

In any arrangement, the plunger may have an enlarged portion in which the resilient annular member is located, the enlarged portion preferably being a bush located at the leading end of the plunger.

Devices according to the invention can be supplied as actuators for fitment to delivery devices of a wide range of types. Alternatively, the devices can themselves be delivery devices.

Devices according to the invention may be linearly-operating devices or actuators, or actuators or devices producing a combined linear and rotational output movement.

Embodiments of the invention will now be described by way of example with reference to the drawings of this specification, in which:

FIG. 1 is a perspective view of an assembly of a delivery device for ophthalmic lenses and an actuator which is an embodiment of the present invention;

FIG. 2 corresponds to FIG. 1 but shows the delivery device and actuator disassembled;

FIG. 3 corresponds to FIG. 2 but shows only the actuator;

Figure 3:
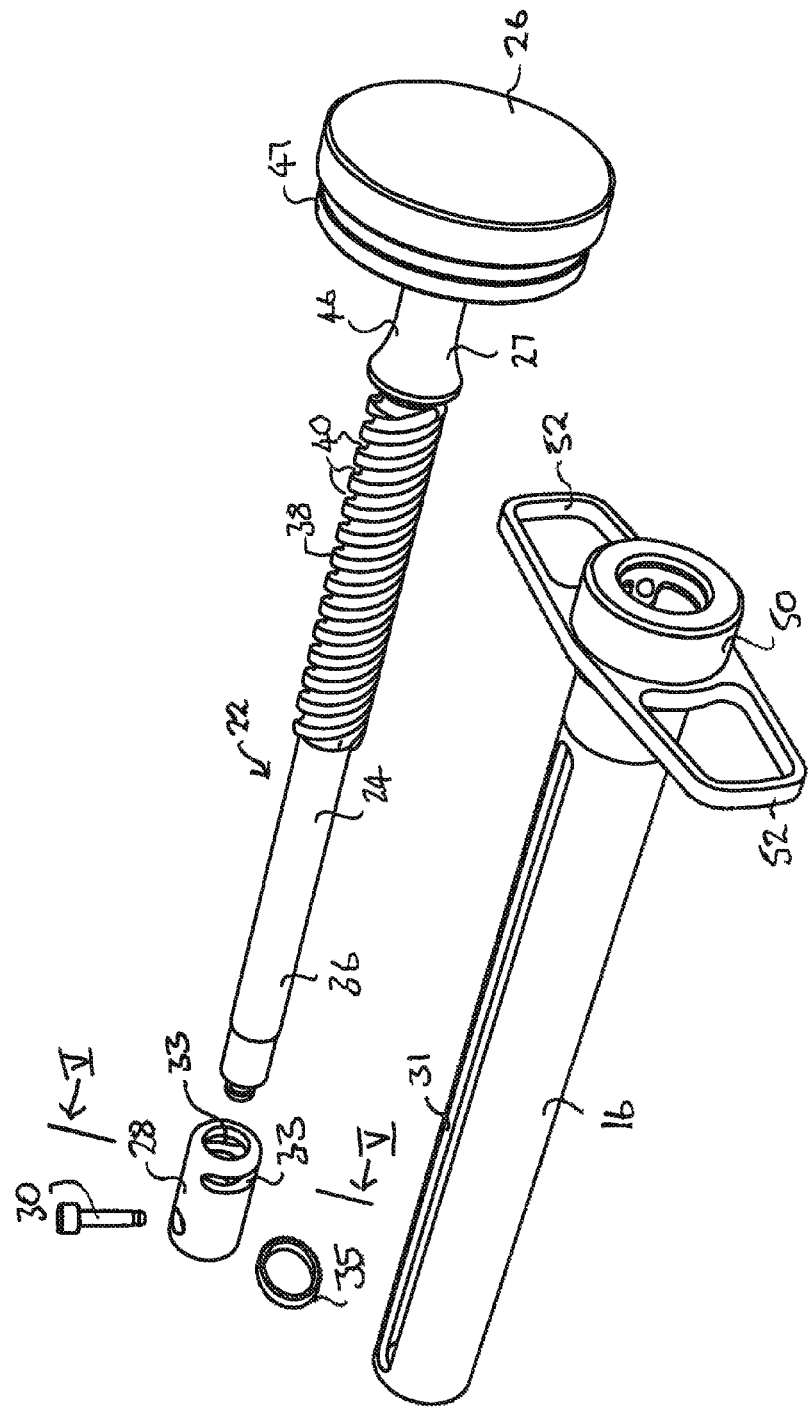
Figure 4:
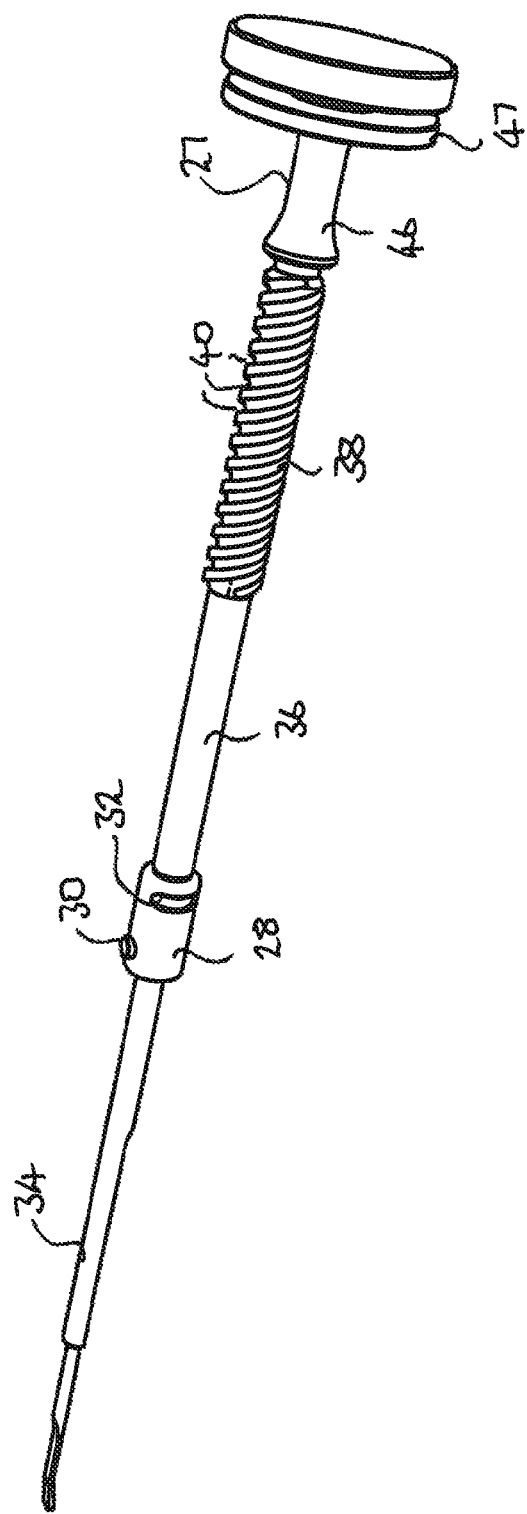
FIG. 4 is a perspective view showing a plunger and attached delivery needle of the actuator of FIG. 3.
Figure 11:
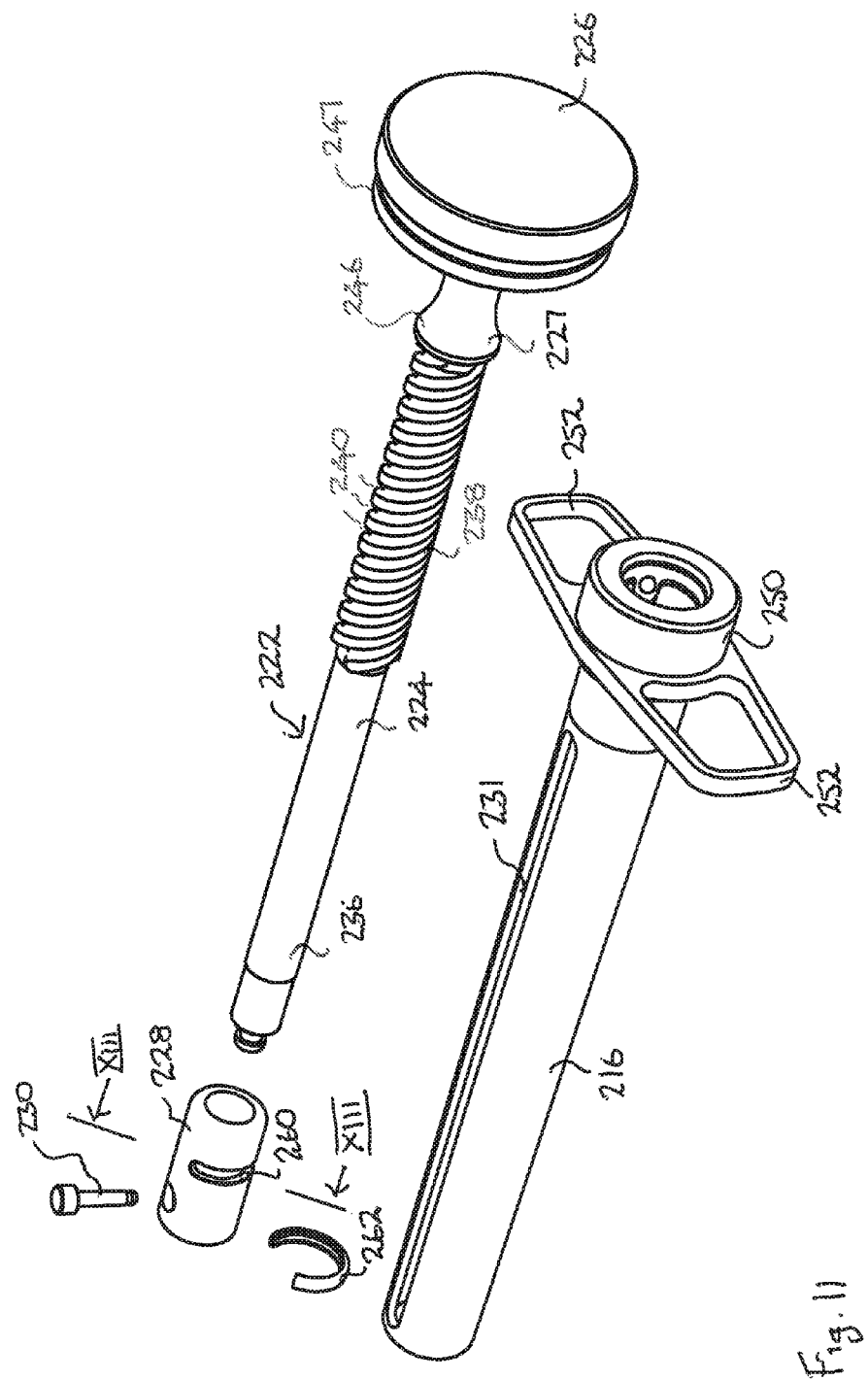
Figure 12:
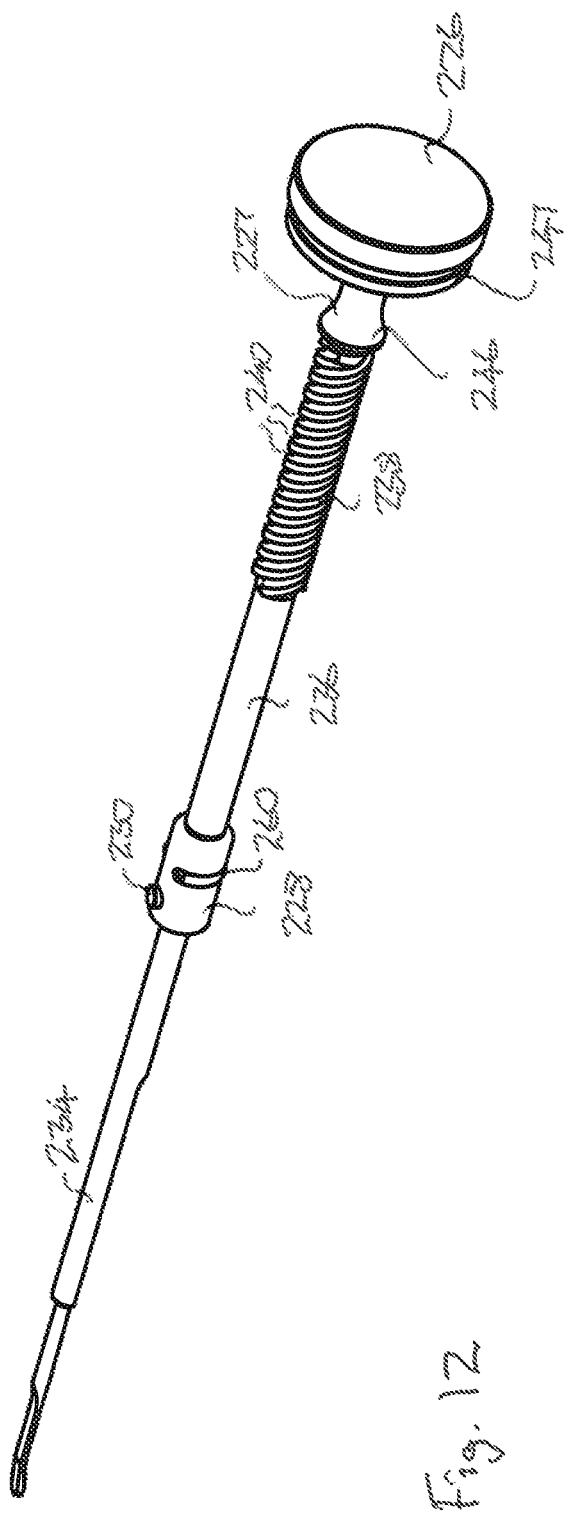
Figure 13:
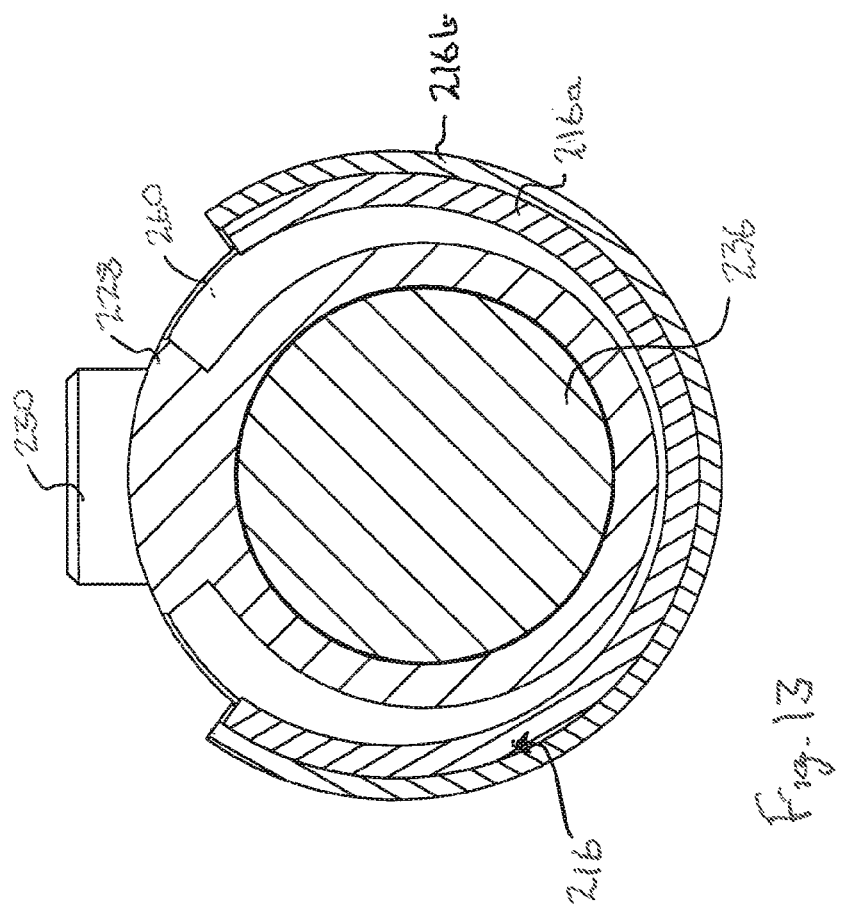

FIG. 11 corresponds to FIG. 3 but shows the actuator of another embodiment;

FIG. 12 corresponds to FIG. 4 but shows the plunger and delivery needle of the actuator of FIG. 11; and FIG. 13 is a cross-section on the line XIII-XIII on FIG. 11.

Figure 1:
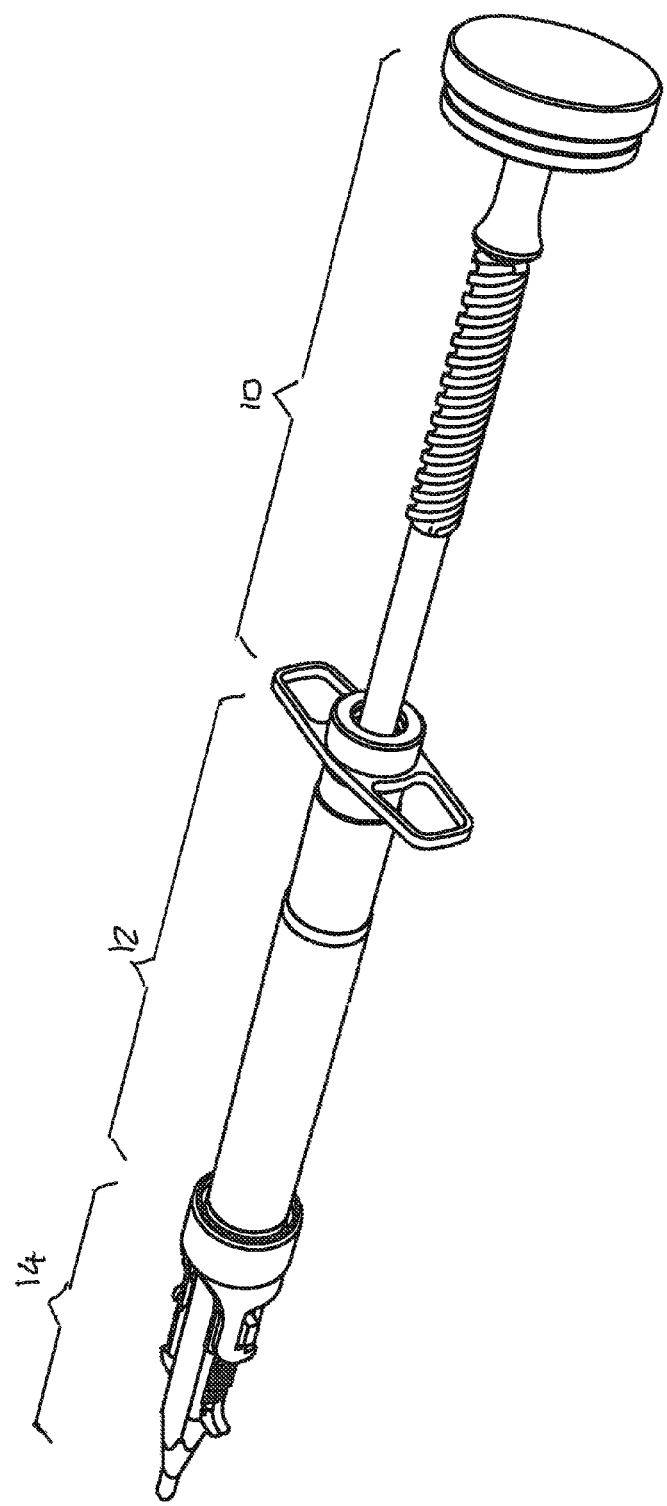

FIG. 1 of the drawings shows an actuator indicated generally at 10 fitted to a delivery device 12 of known type. The delivery device is fitted at its forward end with a lens cartridge 14, also of known type, which contains a rolled or folded lens located in a tapering cavity. The lens is delivered to a patient's eye through an opening in the tip of the cartridge 14.

Figure 2:
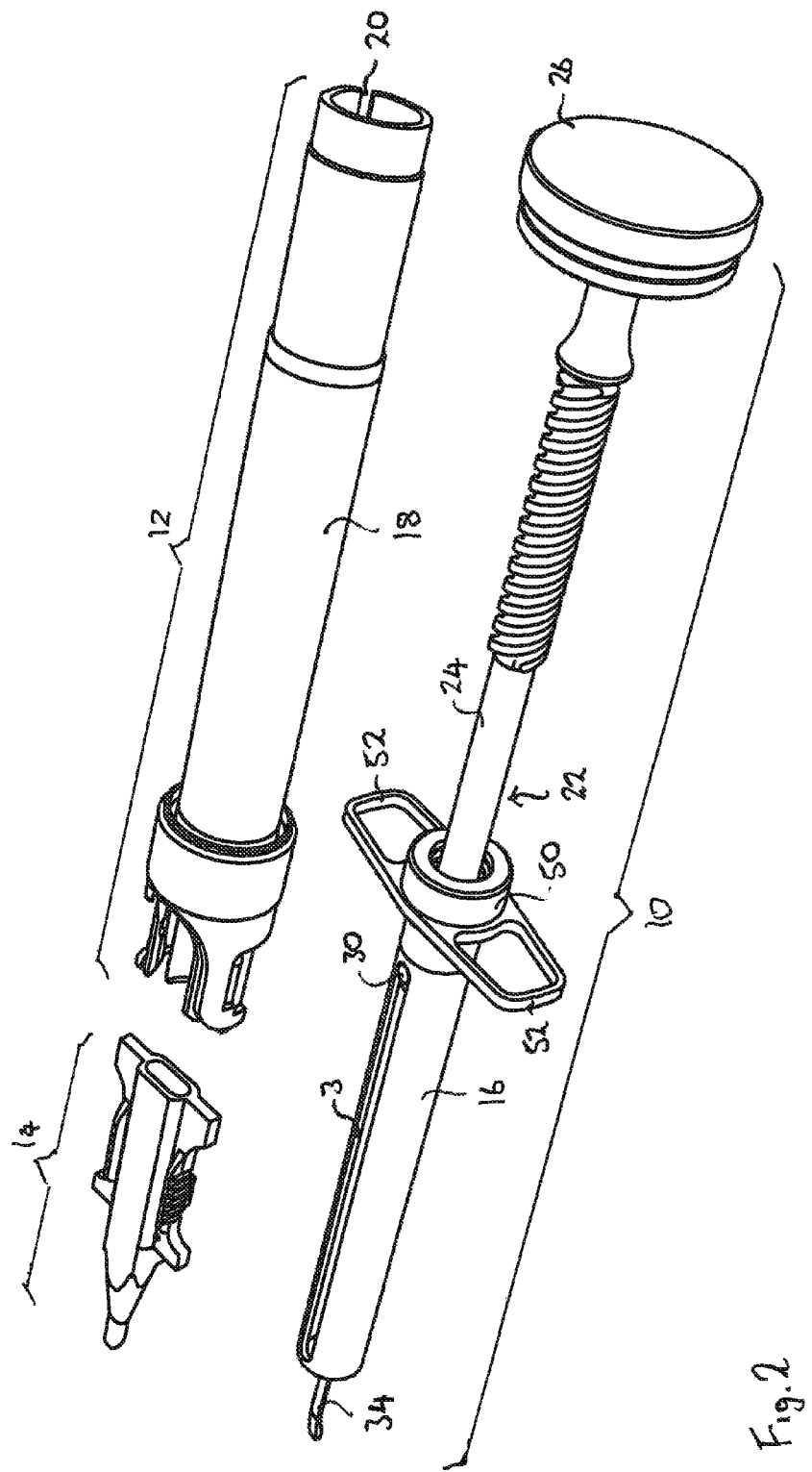

FIG. 2 shows the assembly of FIG. 1 with the actuator 10 disassembled from the delivery device 12 and the lens cartridge 14 dismounted from the delivery device. It will also be seen from FIG. 2 that the actuator 10 comprises a barrel 16 which fits inside a sleeve 18 of the delivery device 12, the barrel 16 and sleeve 18 being secured together by a bayonet connection consisting of a slot 20 in the sleeve 18 and a pin (not visible in the drawings) on the barrel 16.

Figure 5:
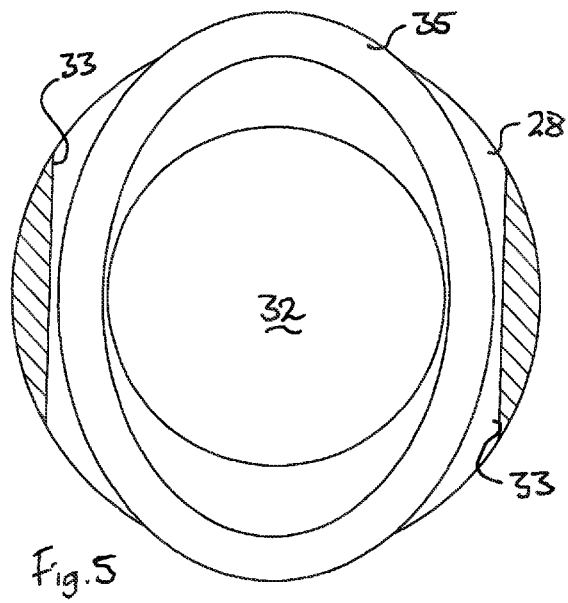
FIG. 5 is a section on the line V-V on FIG. 3.
Figure 6:
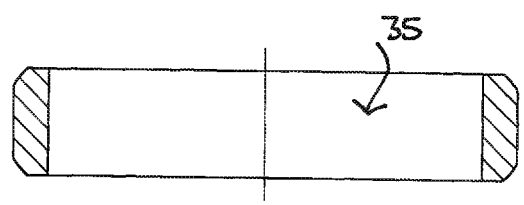
FIG. 6 is a diametral section of a resilient annulus shown in FIG. 5.

FIGS. 2 to 4 of the drawings also show that the actuator 10 comprises a plunger 22 which is slidable in the barrel 16. The plunger 22 (shown in more detail in FIG. 3) comprises a stem 24 which terminates at its rearward end in a cylindrical head 26, forwardly of which is located a mushroom-shaped collar 27 which is described in more detail hereinafter. The stem 24 terminates at its forward end in a cylindrical bush 28 which is a sliding fit in the interior bore of the barrel 16, the bush 28 being made from a suitable plastics material such as a polyetheretherketone (PEEK). The bush 28 is freely rotatable on the stem 24 and carries a pin 30 which is received in a longitudinal slot 31 in the barrel 16 to constrain the bush against rotational movement relative to the barrel. The bush 28 has a diametral transverse passage 32 which extends through the bush to produce a pair of opposed slots 33 in the cylindrical outer wall of the bush, each slot extending over an arc subtending an angle of about 120 degrees at the axis of the cylinder. The passage 33 receives a resistant annulus 35 which is formed from polyetheretherketone (PEEK) material. Any other suitable material could be used instead. The resilient annulus 35 is of rectangular cross-section with radiussed outer edges. It is circular in plan in its relaxed state. The annulus 35 is located in the passage 32, as shown in FIG. 5 of the drawings. The dimensions of the passage 32 and the annulus 35 are chosen so that the annulus is distorted by the wall portions of the cylindrical bush lying between the slots 33 into an oval shape, as shown in FIG. 5 of the drawings. The distortion of the annulus 35 into the oval shape results in end portions of the annulus located at opposite ends of its major axis protruding from respective ones of the slots 33 and thereby making contact with the inner surface of the board 16 when the device is assembled.

A delivery needle 34 is mounted at its rearward end on the bush 28, the needle being shaped to be received in the lens cartridge 14 in order to make contact with a folded or rolled lens and to deliver the lens from the cartridge into a patient's eye as the needle is moved forwards as a result of forward movement of the plunger 22 in the barrel 16. FIG. 4 of the drawings shows separately the assembly of the plunger 22 and the delivery needle 34.

Figure 8:
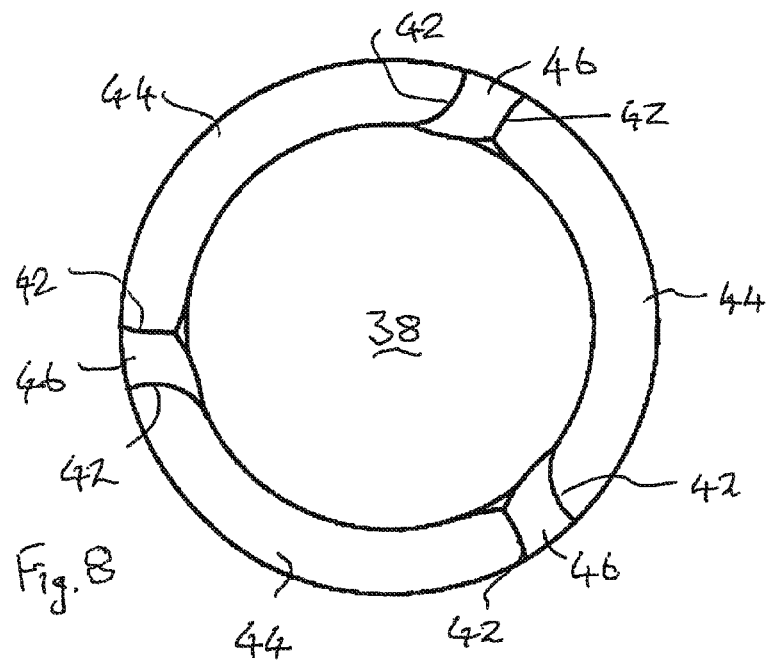
FIG. 8 is a cross-section on the line VIII-VIII on FIG. 7.

The stem 24 of the plunger 22 has a plain forward portion 36, an intermediate portion 38 having a three-start thread formed by three helical grooves 40 of U-shaped transverse section, and a plain rearward portion on which the mushroom-shaped collar 27 is mounted. For reasons which will become evident hereinafter, the grooves 40 widen at their open, forward ends into flared portions 42 which terminate in respective circumferential openings 44 which extend over arcs of about 100 degrees between rounded ends of the inter-groove ridges 46 which extend over arcs of about 20 degrees, as will be evident from FIG. 8 of the drawings. In a modification, the plain forward portion 36 of the plunger stem 24 is omitted and the stem 24 is threaded over its entire length as for the intermediate portion 38 described.

The collar 27 has a hollow stem portion 46 and an annular head portion 47. The plain rearward portion of the stem 22 of the plunger 24 passes through the hollow stem portion 46 so the collar is freely rotatable on the stem 22. The annular head portion 47 has a cross-section very similar to that of the head 26 of the plunger 24 and can be brought into abutment with the underside of the head when urged rearwardly on the stem 22. The intermediate threaded portion 38 of the stem 24 has a cross-section that is greater than the bore of the stem portion 46 of the collar 27 which is thus captive but freely rotatable on the plain rearward portion of the stem 24 of the plunger 22.

The barrel 16 terminates at its rearward end in a cylindrical cup 50, just forwardly of which a pair of outwardly-extending ears 52 protrude one to each side. The ears 52 allow the actuator to be held in one hand by a user with the user's first and second fingers behind the ears and the user's thumb resting on the head 26 of the plunger 22.

The cup 50 receives a clutch mechanism 54 which is operative to provide coupling between the plunger 22 and the barrel 16 of the actuator 10. The clutch mechanism 54 is arranged coaxially around the plunger 22, as can be best seen in FIG. 7 of the drawings which also shows the rearward end of the barrel 16 and a portion of the plunger 22.

The clutch mechanism 54 includes a PTFE friction-reducing washer 56, an annular support member 58, an annular driven member 60 and an end cap 62 which is a press-fit in the rearward end of the cup 50 and is secured against rotation relative thereto. The stem 24 of the plunger 22 extends coaxially through the washer 56, support member 58, driven member 60 and end cap 62.

The annular support member 58 is formed with three circumferential turrets 64, each extending over an arc of approximately 90 degrees. Three arcuate gaps 66 each extending over arcs of about 30 degrees lie between the turrets 64. Each turret 64 has in it a recess 68 of elongate transverse section. A clutch spring 70 is seated in each recess 68, each spring 70 consisting of a rectangular-section ring of resilient plastics material. The springs 70 are circular in plan when in a relaxed condition but can be resiliently deformed to be oval in plan. Springs of this type have been found to be particularly simple to form and their rates readily determined and controlled.

The springs 70 act on a forward annular face 72 of the driven member 60 and therefore act to bias the support 58 and the driven member 60 apart in the axial direction.

Figure 7:
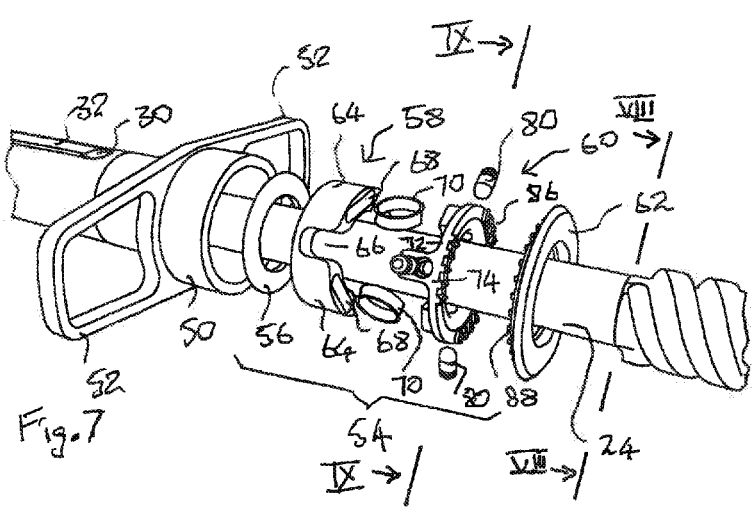
FIG. 7 is an exploded perspective view of a clutch mechanism of the actuator of FIG. 3.
Figure 9:
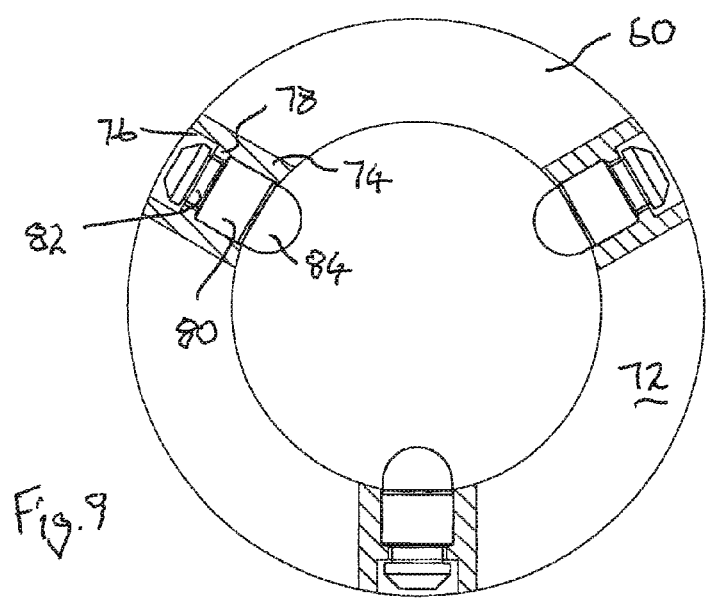
FIG. 9 is a cross-section on the line IX-IX on FIG. 7.

The driven member 60 is formed on its forward face 72 with three equidistantly-spaced turrets 74, each extending over an arc of approximately 30 degrees, as will be seen most clearly in FIG. 7 of the drawings. The turrets 74 of the driven member are received in the gaps 66 between the turrets 64 of the support member 58. As can be seen from FIG. 9, each turret 74 has a radial bore 76 having an internal circumferential ridge 78. Each bore 76 receives a respective drive pin 80 which has a circumferential groove 82 which is a snap-fit over the corresponding ridge 78 in the respective bore 76. Each pin 80 has a hemispherical inner end 84 which projects radially inwardly from the driven member 60.

The driven member 60 is formed on its rearward annular face with a series of castellations 86 which engage a series of corresponding castellations 88 formed on the forward face of the end cap 62. The springs 70 therefore bias the series of castellations 86, 88 into engagement with each other and lock the driven member 60 and end cap 62 together against relative rotational movement. The axial length of the cup 50 is chosen such that the springs 70 are slightly deformed from their circular shapes in this condition of the clutch mechanism, thus providing a small preloading force.

The hemispherical end portions 84 of the pins 80 which protrude radially inwardly are positioned so as to be received in a respective one of the grooves 40 formed by the threads of the threaded portion 38 of the plunger 24, entry of the pins into the grooves being facilitated by the flared end portions 42 of the grooves 40, when the plunger stem has a plain forward portion 36.

The support member 58, springs 70 and pins 80 are formed from a suitable engineering plastics material such as a polyetheretherketone (PEEK). The driven member 60 may be formed from a polyetherimide such as that sold under the name ULTEM®. Except as specifically mentioned otherwise, the actuator is made from a suitable titanium alloy. Stainless steel could be used instead. If not formed from a polyetherimide as mentioned, the driven member may be made from a suitable titanium alloy, or stainless steel.

The clutch mechanism operates as follows. In the disengaged condition of the mechanism already referred to, the driven member 60 is urged by the springs 70 rearwardly relative to the end cap 62. The castellations 86, 88 are thereby brought into engagement and the driven member 60 and the support member 58 are locked against rotation relative to the end cap 62. In this condition of the clutch, the forward, plain portion 36 of the plunger 24, if present, can pass unimpeded through the clutch mechanism and the plunger 24 can be advanced correspondingly axially of the barrel 16.

If the plunger 24 is advanced through the barrel to an extent that its threaded portion 38 passes into the clutch mechanism, the pins 80 engage in respective grooves 40 of the threaded portion 38. If no plain plunger portion is present, the pins 80 are already in engagement with the grooves 40. Whilst the clutch mechanism remains engaged, the plunger 22 can be advanced further through the barrel 16 if it is rotated to allow the pins 80 to pass helically along the grooves 40 of the thread. This is achieved in the absence of any significant axial load on the plunger 22.

If however a significant axial load is placed on the plunger 22, the pins 80, rather than passing helically along the grooves 40, engage with the walls of the grooves with the result that the load on the plunger 22 is transferred to the driven member 60 which is shifted axially against the bias of the springs 70 such that the castellations 86, 88 disengage to allow the driven member 60 to rotate relative to the end cap 62. The plunger 22 can now be advanced forwardly relative to the barrel 16 for so long as the axial load is maintained.

Figure 10:
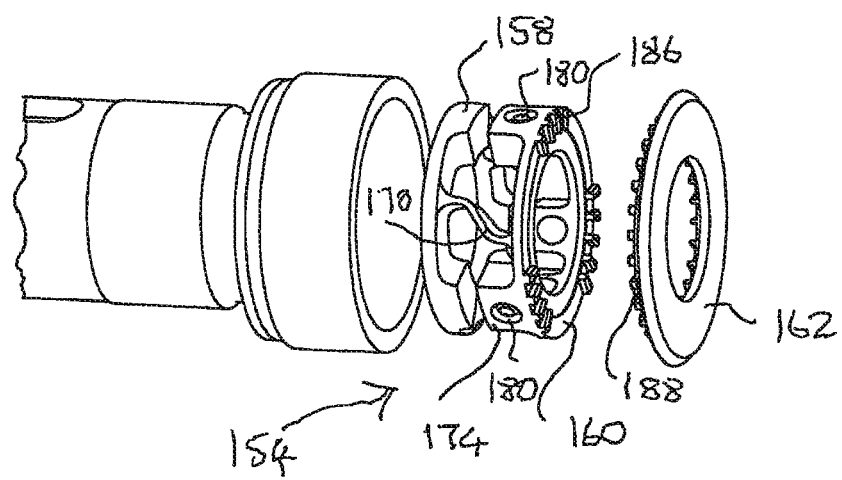
FIG. 10 is an exploded perspective view of a modified clutch mechanism.

FIG. 10 shows a modified clutch mechanism, the parts of which corresponding to parts of the mechanism 54 are indicated by reference numerals increased by "100" compared with the reference numerals used for the parts of the mechanism 54.

The modified clutch mechanism 154 comprises a support member 158 and a driven member 160 which are formed integrally as a plastics moulding and which are joined by integral resilient twisted straps 170 corresponding to the springs 70. The driven member 160 has three circumferentially-spaced turrets 174 which support drive pins 180 in a manner corresponding exactly to that described hereinbefore for the clutch mechanism 54. The rearward face of the driven member 160 is formed with castellations 186 which engage with castellations 188 on the forward face of the end cap 162.

The modified clutch mechanism operates in a very similar manner to the mechanism 54, except that the resilient loading is provided by the twisted straps 170 and not the springs 70.

In a further modification (not shown in the drawings), a rolling element thrust bearing such as a needle roller or ball race thrust bearing replaces the PTFE friction-reducing washer 56 shown in FIG. 7 of the drawings. Such a bearing can reduce friction between the support member 58 and the interior of the cup 50 to a greater extent than the washer 56. A corresponding modification may also be made to the actuator described with reference to FIG. 10 of the drawings.

FIGS. 11 and 12 of the drawings show an actuator which is a modification of the actuator shown in FIGS. 2 to 4 of the drawings. Features of the actuator of FIGS. 11 and 12 which correspond to those of the actuator of FIGS. 2 to 4 are indicated by reference numerals which are increased by "200" compared with the reference numerals used in FIGS. 2 to 4. The features which are identical will not be described further in this specification.

As can be seen from FIG. 13 of the drawings, the bush 228 of the actuator shown in FIGS. 11 and 12 has a recess 260 which extends over approximately 330 degrees of the periphery of the bush.

FIGS. 11 to 13 of the drawings show that the recess 260 receives a C-shaped resilient element 262, which is formed laminated in two layers, an inner layer 216a being of titanium alloy to provide a suitable spring rating and an outer 216b being of PEEK material provide a bearing surface which is in contact over its outer periphery with the interior surface of the barrel 216 of the actuator shown in FIGS. 11 to 13.

The dimensions of the recess 260 and the C-shaped member 262 are chosen so that the C-shaped member is in contact with the interior of the barrel 216 over the portion extending between the respective edges of the slot 231. In FIG. 13, the barrel is not shown so the C-shaped element 262 is in its relaxed condition, in which it protrudes as shown from the recess 260. The C-shaped member thus provides a similar degree of resistance to the movement of the plunger in the barrel as does the resilient element 35 shown in FIGS. 2 to 4 of the drawings.

The use of the actuators shown in FIGS. 1 to 9, FIG. 10 and FIGS. 11 to 13 in connection with a delivery device for the insertion of a rolled ophthalmic lens into the human eye will now be described.

An actuator having a clutch mechanism 54 as shown in FIG. 7 or a clutch mechanism 154 as shown in FIG. 10 is assembled to a delivery device 12 as shown in FIGS. 1 and 2, the delivery device being fitted with a lens cartridge 14 as also shown in FIGS. 1 and 2. Either device may have a resilient element as described with reference to FIGS. 1 to 10 or a resilient element as described with reference to FIGS. 11 to 13. Advancement of the plunger 22 or 222 of the actuator 10 through the barrel 16 or 216 of the actuator causes the delivery needle 34 or 234 to pass into the lens cartridge 14 (in FIG. 2) with the result that the rolled ophthalmic lens contained in the cartridge 14 is delivered outwardly through the aperture in the tip of the cartridge 14.

During the first portion of the stroke of movement of the plunger 22 or 222, any plain, unthreaded forward portion 36 or 236 of the stem 24 or 224 of the plunger 22 or 222 passes through the clutch mechanism 54 or 154 without contact, allowing the delivery needle 34 or 234 to be advanced rapidly and with little resistance, as is desirable during the initial phase of lens delivery before the tip of the needle 34 or 234 contacts the rolled lens in the cartridge 14. During this initial phase, the surgeon may hold the delivery device and actuator with his first and second fingers behind the ears 52 or 252 and his thumb on the head 26 or 226.

In the next phase of the delivery process, the threaded portion 38 of the plunger stem 24 or 224 engages, or is already engaged, with the clutch mechanism 54 or 154 as described above. The surgeon now has the option as he wishes either to continue the forward movement of the plunger in the actuator barrel in a one-handed operation which results in an axial loading on the plunger 22 or 222 with the effect that the clutch mechanism 54 or 154 disengages and the plunger can continued to be moved forwardly through the delivery device. Alternatively, if he wishes, the surgeon can continue to hold the barrel 16 or 216 of the actuator in one hand and then, by twisting the head 26 or 226 of the plunger 22 or 222 advance the needle to deliver the lens from the cartridge 14. In this case, in the absence of substantial axial loading on the plunger, the clutch 54 or 154 remains engaged and the twisting movement of the plunger stem 24 or 224 results in further forward movement of the plunger with the pins 80 or 180 of the clutch mechanism 54 or 154 engaged in the grooves 40 or 240 of the threaded portion of the plunger stem. This allows the surgeon, according to his choice, to control the second stage of the insertion operation in a two-handed operation involving a rotary motion of the plunger 22 or 222 relative to the barrel 16. The particularly advantageous feature of allowing the surgeon at his choice to employ a one-handed or a two-handed technique of lens delivery is therefore provided by the actuator of the present invention.

It is desirable that, during the insertion phase described, if the surgeon relaxes or relieves his grip on the plunger, the plunger does not move rearwardly under its own weight. The reason for this being desirable is that it prevents the needle 34 or 234 from losing contact with the lens, such loss of contact leading possibly to damaging contact with one or both of the haptics of the lens on re-engagement therewith.

In the device described with references to FIGS. 1 to 10, the contact between the opposed ends of the distorted annulus 35 and the interior of the barrel 16 provides a suitable frictional restraining force which can be determined by an appropriate choice of dimension and material of the annulus. In the device described with reference to FIGS. 11 to 13, the contact between the C-shaped member 262 and the interior of the barrel 216 provides a similar frictional force which can again be determined by an appropriate choice of dimension and material by the C-shaped member 262. The plunger and needle are in each case thereby prevented from "falling-back" in the barrel when the forward force is relieved or removed.

It is also desirable that the surgeon be able to return the plunger 22 or 222 quickly and easily to its rearward or retracted position after completion of an insertion procedure, to ready it for the next insertion operation. In all the embodiments described, this can be achieved readily and rapidly by placing two fingers on the forward-facing surface of the head 47 or 247 of the collar 27 or 227 and pulling the head rearwardly into contact with the head 26 or 226 of the plunger 22 or 222. Continued rearward movement of the collar will result in rearward movement of the plunger which, as a result of the engagement of the threaded portion 38 or 238 with the barrel 16 or 216 by way of the clutch mechanism 54 or 154, will rotate within the collar 27 or 227. Rotation of the plunger in the surgeon's hands or the need to apply a rotatory movement to the plunger are avoided. Convenience of use is thereby improved.

The invention claimed is:

1. A device for use in delivery of ophthalmic lenses, the device comprising a barrel, a plunger with a plunger body having a proximal end and a distal end receivable in the barrel and movable between a first relatively withdrawn position and a second more advanced position and, the plunger body having a terminal head portion positioned at the proximal end, the terminal head portion being engageable manually for movement of the plunger body from the first position to the second position, the plunger body further having a coupling means providing part of a screw-threaded connection between a portion of the plunger body and the barrel and whereby the plunger body rotates relative to the barrel in moving from its second position to its first position, the plunger body further having a rotatable portion positioned towards the proximal end of the plunger body relative to the coupling means, the rotatable portion being distal to the terminal head portion and rotatable relative to the coupling means of the plunger body and being engageable manually by a user for linear movement in a withdrawal direction whilst allowing rotation of the plunger body relative to the barrel.

2. A device according to claim 1, in which the rotatable portion has at least one outwardly-extending portion for manual engagement by a user.

3. A device according to claim 1, in which one said outwardly-extending portion comprises a collar extending around the plunger.

4. A device according to claim 1, in which the terminal head portion has a larger cross-section than that of the plunger, and the rotatable portion is located adjacent the head portion.

5. A device according to claim 4, in which the rotatable portion is movable into abutment with the head portion in order to urge the plunger in a direction from the second to the first position.

* * * * *